US00PP23039P2

(12) United States Plant Patent
Hooijman

(10) Patent No.: US PP23,039 P2
(45) Date of Patent: Sep. 18, 2012

(54) ROSE PLANT NAMED 'ESM MANGO'

(50) Latin Name: *Rosa hybrida*
Varietal Denomination: Esm Mango

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 13/134,374

(22) Filed: Jun. 6, 2011

(51) Int. Cl.
*A01H 5/00* (2006.01)

(52) U.S. Cl. ..... Plt./134

(58) Field of Classification Search ..... Plt./134
See application file for complete search history.

*Primary Examiner* — Kent L Bell
(74) *Attorney, Agent, or Firm* — C. A. Whealy

(57) ABSTRACT

A new and distinct cultivar of Rose plant named 'Esm Mango', characterized by its strong and upright flowering stems; vigorous growth habit and high productivity; freely flowering habit; light yellow-colored flowers arranged in upright sprays; excellent postproduction longevity; and resistance to *Botrytis*.

1 Drawing Sheet

Botanical designation: *Rosa hybrida*.
Cultivar denomination: 'ESM MANGO'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'Esm Mango'.

The new Rose plant is a product of a planned breeding program conducted by the Inventor in El Quinche, Pichincha, Ecuador. The objective of the breeding program was to develop new freely-flowering cut flower Rose varieties with novel and attractive flower colors and excellent postproduction longevity.

The new Rose plant originated from a cross-pollination made by the Inventor in February, 2002 of a proprietary Rose selection identified as code name Line 90, not patented, as the female, or seed, parent with a proprietary Rose selection identified as code name Line 10, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in March, 2003.

Asexual reproduction of the new Rose plant by cuttings at El Quinche, Pichincha, Ecuador since November, 2004, has shown that the unique features of this new Rose plant are stable and reproduced true to type in successive generations of asexual reproduction.

SUMMARY OF THE INVENTION

Plants of the new Rose have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Esm Mango'. These characteristics in combination distinguish 'Esm Mango' as a new and distinct Rose plant:

1. Strong and upright flowering stems.
2. Vigorous growth habit and high productivity.
3. Freely flowering habit.
4. Light yellow-colored flowers arranged in upright sprays.
5. Excellent postproduction longevity.
6. Resistance to *Botrytis*.

Plants of the new Rose differ from plants of the female parent selection in the following characteristics:

1. Plants of the new Rose are taller than plants of the female parent selection.
2. Plants of the new Rose produce more flowering stems than plants of the female parent selection.
3. Plants of the new Rose have larger flowers than plants of the female parent selection.
4. Plants of the new Rose and the female parent selection differ in flower color as plants of the female parent selection have light pink-colored flowers.
5. Flowers of plants of the new Rose are longer lasting than flowers of plants of the female parent selection.

Plants of the new Rose differ from plants of the male parent selection in the following characteristics:

1. Plants of the new Rose are taller than plants of the male parent selection.
2. Plants of the new Rose produce more flowering stems than plants of the male parent selection.
3. Flowers of plants of the new Rose are arranged in sprays whereas flowers of plants of the male parent selection are solitary.
4. Plants of the new Rose and the male parent selection differ in flower color as plants of the male parent selection have dark yellow-colored flowers.

Plants of the new Rose can be compared to plants of Rose 'Sun City', not patented. In side-by-side comparisons conducted in El Quinche, Pichincha, Ecuador, plants of the new Rose differed from plants of 'Sun City' in the following characteristics:

1. Plants of the new Rose were taller and broader than plants of 'Sun City'.
2. Plants of the new Rose were more vigorous than plants of 'Sun City'.
3. Plants of the new Rose had stronger flowering stems than plants of 'Sun City'.

4. Plants of the new Rose were more freely branching than plants of 'Sun City'.
5. Plants of the new Rose flowered six days earlier than plants of 'Sun City'.
6. Plants of the new Rose had lighter yellow-colored flowers than plants of 'Sun City'.
7. Flowers of plants of the new Rose were longer lasting than flowers of plants of 'Sun City'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the upper left of the sheet comprises a side perspective view of a typical flowering stem of 'Esm Mango'.

The photograph at the upper right of the sheet is a close-up view of a typical flower of 'Esm Mango'.

The photograph at the bottom left of the sheet is a close-up view of a typical flowering spray of 'Esm Mango'.

The photographs at the bottom right of the sheet are close-up views of the upper and lower surfaces of typical leaves of 'Esm Mango'.

DETAILED BOTANICAL DESCRIPTION

Plants of the new Rose have not been observed under all possible environmental conditions and cultural practices. The phenotype may vary somewhat with variations in environment conditions such as temperature and light intensity, without, however, any variance in genotype. The aforementioned photographs, following observations and measurements describe plants grown in 10-liter containers in a polyethylene-covered greenhouse in El Quinche, Pichincha, Ecuador and under typical hydroponic Rose production practices. Plants were pinched about 13 to 14 weeks after planting. Plants were 3.5 years old when the photographs and description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'Esm Mango'.

Parentage:

*Female, or seed, parent*.—Proprietary seedling selection of *Rosa hybrida* identified as code name Line 90, not patented.

*Male, or pollen, parent*.—Proprietary seedling selection of *Rosa hybrida* identified as code name Line 10, not patented.

Propagation:

*Type*.—By cuttings.

*Time to initiate roots*.—About seven to ten days at 26° C. to 30° C.

*Time to produce a rooted young plant*.—About four to five weeks at 22° C. to 26° C.

*Root description*.—Fibrous, fine; close to N200A in color.

*Rooting habit*.—Freely branching; dense.

Plant description:

*Plant form*.—Upright plant habit; strong and upright flowering stems.

*Growth habit*.—Vigorous; freely basal branching habit; dense and bushy growth habit; highly productive with about 14.4 flowering stems developing per plant per year.

*Plant height*.—About 115 cm.

*Plant width* (*spread*).—About 59 cm.

*Lateral branches* (*peduncles*).—Length: About 84 cm. Diameter: About 6.5 mm. Internode length: About 4.9 cm. Texture: Smooth, glabrous. Color: Close to 146A; with development, color becoming closer to N199A. Thorns: Density: Medium density. Shape: Triangular with sharp acuminate apices; slightly incurved. Height: About 1.1 cm. Length, at base: About 1.1 cm. Color, immature: Close to 173A. Color, mature: Close to 164A and 152C.

Foliage description:

*Arrangement*.—Alternate; compound with typically five leaflets per leaf.

*Leaf length*.—About 14.5 cm.

*Leaf width*.—About 11.9 cm.

*Terminal leaflet length*.—About 6.6 cm.

*Terminal leaflet width*.—About 3.9 cm.

*Lateral leaflet length*.—About 5.9 cm.

*Lateral leaflet width*.—About 3.6 cm.

*Leaflet shape*.—Oval.

*Leaflet apex*.—Acute.

*Leaflet base*.—Attenuate.

*Leaflet margin*.—Serrate.

*Leaflet texture, upper surface*.—Smooth, glabrous; coriaceous.

*Leaflet texture, lower surface*.—Prickles along leaf axis.

*Leaflet venation pattern*.—Pinnate.

*Leaflet color*.—Developing leaflets, upper surface: Close to 146A. Developing leaflets, lower surface: Between 146B and 148A. Fully expanded leaflets, upper surface: Close to 139A; venation, close to 147C. Fully expanded leaflets, lower surface: Close to 147B; venation, close to 146D.

*Petioles, leaves*.—Length: About 1 cm. Diameter: About 2 mm. Texture, upper and lower surfaces: With prickles. Color, upper surface: Between 143C and 137A. Color, lower surface: Close to 146B.

*Petioles, leaflets*.—Length: About 2.2 cm. Diameter: About 1.1 mm. Texture, upper and lower surfaces: With prickles. Color, upper surface: Close to 147A. Color, lower surface: Close to 146B.

*Stipules*.—Arrangement and appearance: Two, adnate to the petiole, leafy in appearance. Length: About 2.5 cm. Width: About 2.7 mm. Shape: Roughly deltoid. Apex: Acuminate. Base: Truncate. Margin: Serrate, irregular. Texture, upper and lower surfaces: Smooth, glabrous; membranous; pubescence along the margins. Venation pattern: Pinnate. Color, upper surface: Close to 137B. Color, lower surface: Close to 146A.

Flower description:

*Flower type and flowering habit*.—Symmetrical rosette flowers; flowers arranged in terminal sprays; freely flowering habit with about seven flowers per spray.

*Flowering season*.—Year-round under greenhouse conditions; plants begin flowering about 76 days after pinching; in the garden, optimal flowering from spring through autumn; flowering intermittent.

*Spray diameter*.—About 21 cm.

*Spray height*.—About 24 cm.

*Flower diameter*.—About 8 cm.

*Flower depth* (*height*).—About 4 cm.

*Flower longevity on plant*.—About 36 days; flowers persistent.

*Flower longevity as a cut flower*.—Excellent postproduction longevity, flowers last about 11 to 13 days.

*Fragrance*.—Faintly fragrant, pleasant.

*Flower buds*.—Shape: Cupped. Length: About 3.2 cm. Diameter: About 2.3 cm. Color: Between 143A and 144A.

*Petals*.—Quantity: About 35 to 40 per flower; petals imbricate. Length: About 3.3 cm. Width: About 3.7 cm. Shape: Nearly round; transversely ovate. Apex: Blunt to shortly acute. Base: Obtuse. Margin: Entire. Texture, upper and lower surfaces: Smooth, glabrous; papery to coriaceous. Color: When opening, upper surface: Close to 12A; towards the apex, close to 1D. When opening, lower surface: Close to 12A; towards the apex, close to 1D; towards the base, close to 2B. Fully opened, upper surface: Close to 12A; towards the apex, close to 3D. Fully opened, lower surface: Close to 7B; towards the apex, close to 2D.

*Sepals*.—Quantity per flower: Typically five. Length: About 3.6 cm. Width: About 1.3 cm. Shape: Roughly deltoid. Apex: Tapered. Base: Truncate. Margin: Entire; ciliate and/or glandular. Texture, upper and lower surfaces: Coriaceous; pubescence along the margins. Color: When opening, upper surface: Between 146D and 147C. When opening, lower surface: Close to 144A tinted with close to 166A. Fully opened, upper surface: Between 146C and N144D. Fully opened, lower surface: Close to 144A tinted with close to N199C.

*Pedicels*.—Length: About 3.9 cm. Diameter: About 3 mm. Angle: About 40° from vertical. Strength: Strong. Texture: With prickles. Color: Between 146B and 144A.

*Reproductive organs*.—Stamens: Quantity: About 135 per flower. Anther length: About 2.7 mm. Anther shape: Reniform. Anther color: Between N163D and 162C. Filament color: Close to 12A. Pollen amount: Abundant. Pollen color: Close to 163A. Pistils: Quantity: About 87 per flower. Pistil length: About 1.1 cm. Stigma shape: Broadly reniform. Stigma color: Close to 160A. Style length: About 8 mm. Style color: Close to 145B. Receptacle height: About 8 mm. Receptacle diameter: About 1 cm. Receptacle shape: Cup-shaped. Receptacle texture: Smooth, glabrous. Receptacle color: Close to 144A. Fruits: Length: About 2.2 cm. Diameter: About 2.2 cm. Texture: Smooth. Color: Close to 163A. Seeds: Quantity per fruit: About nine. Length: About 5 mm. Diameter: About 5 mm. Texture: Smooth. Color: Close to 153C.

Pathogen/pest resistance: Plants of the new Rose have been observed to be resistant to *Botrytis*. Plants of the new Rose have not been observed to be resistant to pests and other pathogens common to Rose plants.

Temperature tolerance: Plants of the new Rose have been observed to tolerate temperatures ranging from 0° C. to 35° C.

It is claimed:

1. A new and distinct Rose plant named 'Esm Mango' as illustrated and described.

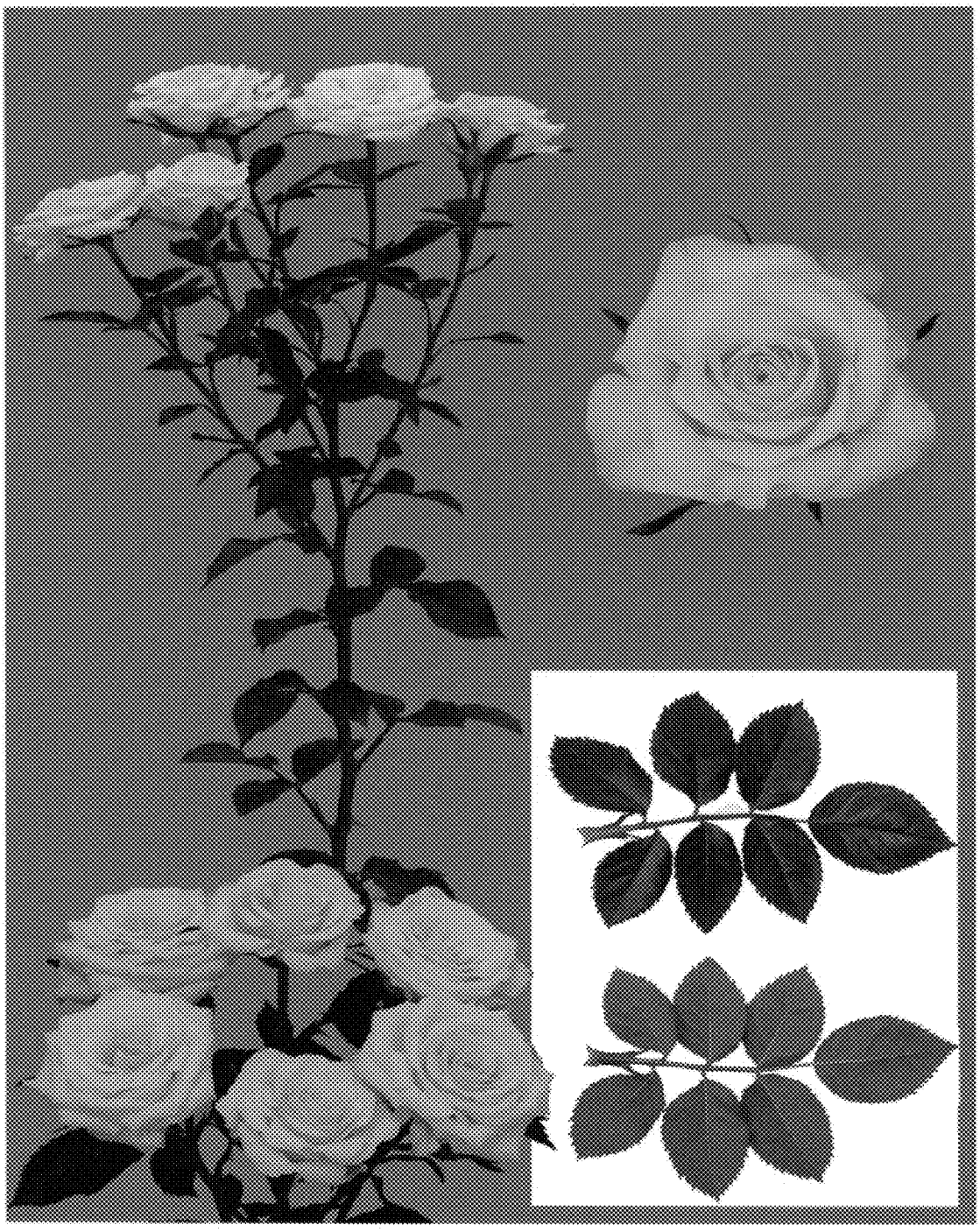

* * * * *